United States Patent [19]

Hounsfield et al.

[11] 4,250,387

[45] Feb. 10, 1981

[54] MEDICAL RADIOGRAPHIC APPARATUS AND METHOD

[75] Inventors: Godfrey N. Hounsfield, Winthorpe; Richard M. Waltham, London, both of England; Daniel J. Pisano, Jr., Barrington; Erlvada A. Olson, Wheeling, both of Ill.

[73] Assignee: EMI Limited, England

[21] Appl. No.: 84,123

[22] Filed: Oct. 12, 1979

[51] Int. Cl.³ .............................................. G03B 41/16
[52] U.S. Cl. ................................. 250/445 T; 250/401; 250/402
[58] Field of Search ................... 250/445 T, 401, 402, 250/416 R

[56] References Cited

U.S. PATENT DOCUMENTS

| 3,940,625 | 2/1976 | Hounsfield | 250/445 T |
| 4,132,654 | 1/1979 | Braun | 250/320 |

*Primary Examiner*—Craig E. Church

*Attorney, Agent, or Firm*—Cooper, Dunham, Clark, Griffin & Moran

[57] ABSTRACT

Computerized tomographic X-ray apparatuses direct X-rays, usually in a fan-shaped distribution, through the body of a patient. In some examples the fan distribution may subtend angles of 50° or more at the source. It has been found that such tubes, particularly of the rotating anode type, tend to have X-ray emission from regions surrounding the focal spot and it is not convenient to use anode shields to eliminate it. This off-focus radiation can present problems, especially when attenuators are used to equalize absorbing paths through the patient, since the off-focus radiation can sometimes be less attenuated than the main beam. It is proposed to correct the signals produced by the X-ray detectors, for off-focus radiation. A profile of off-focus or halo radiation is produced and the attenuation imposed on it is estimated. The estimates are used to suitably modify the signals produced by the X-ray detectors (or signals derived from the detector outputs) so as to correct for the presence of off-focus radiation.

14 Claims, 12 Drawing Figures

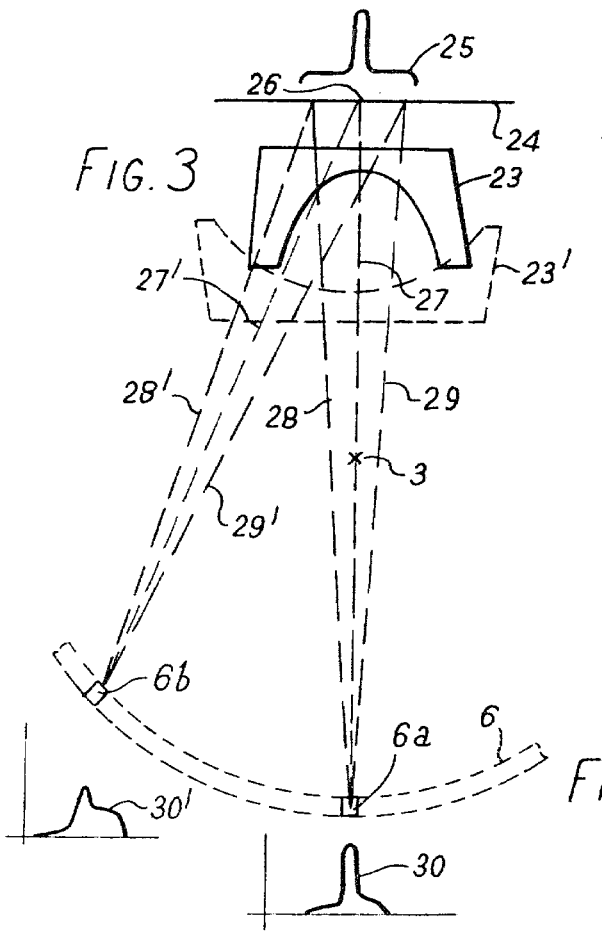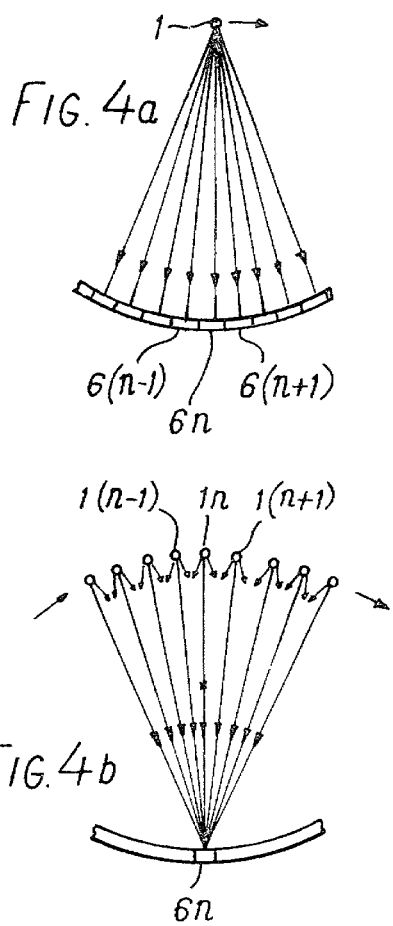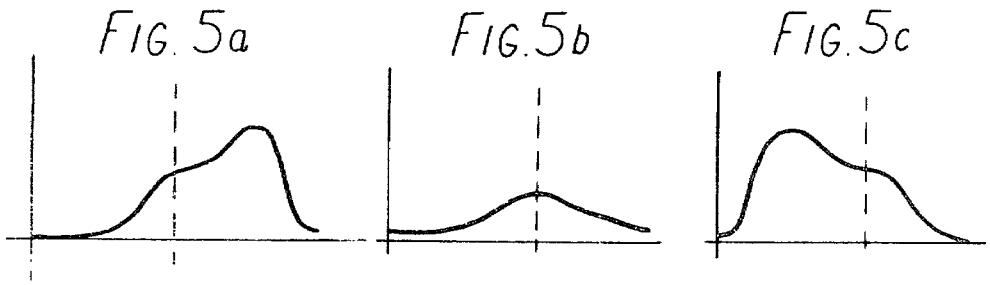

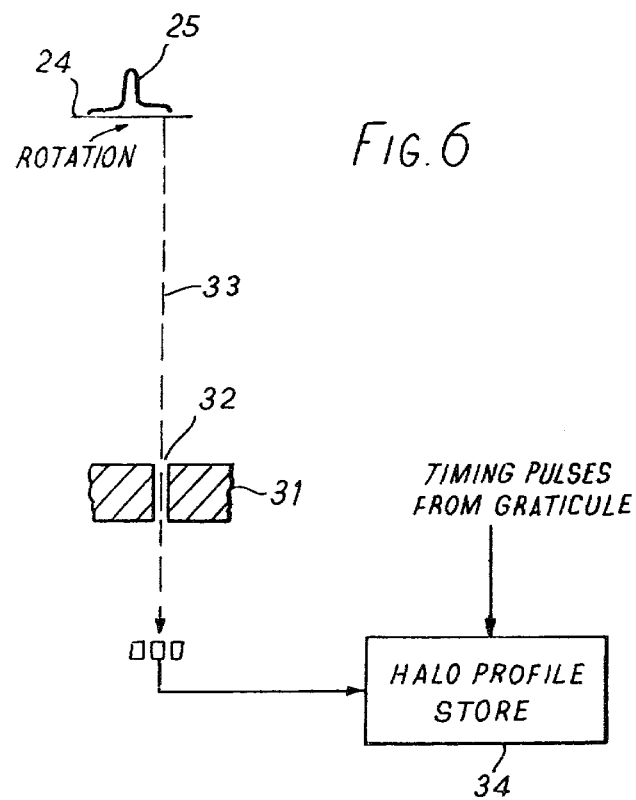

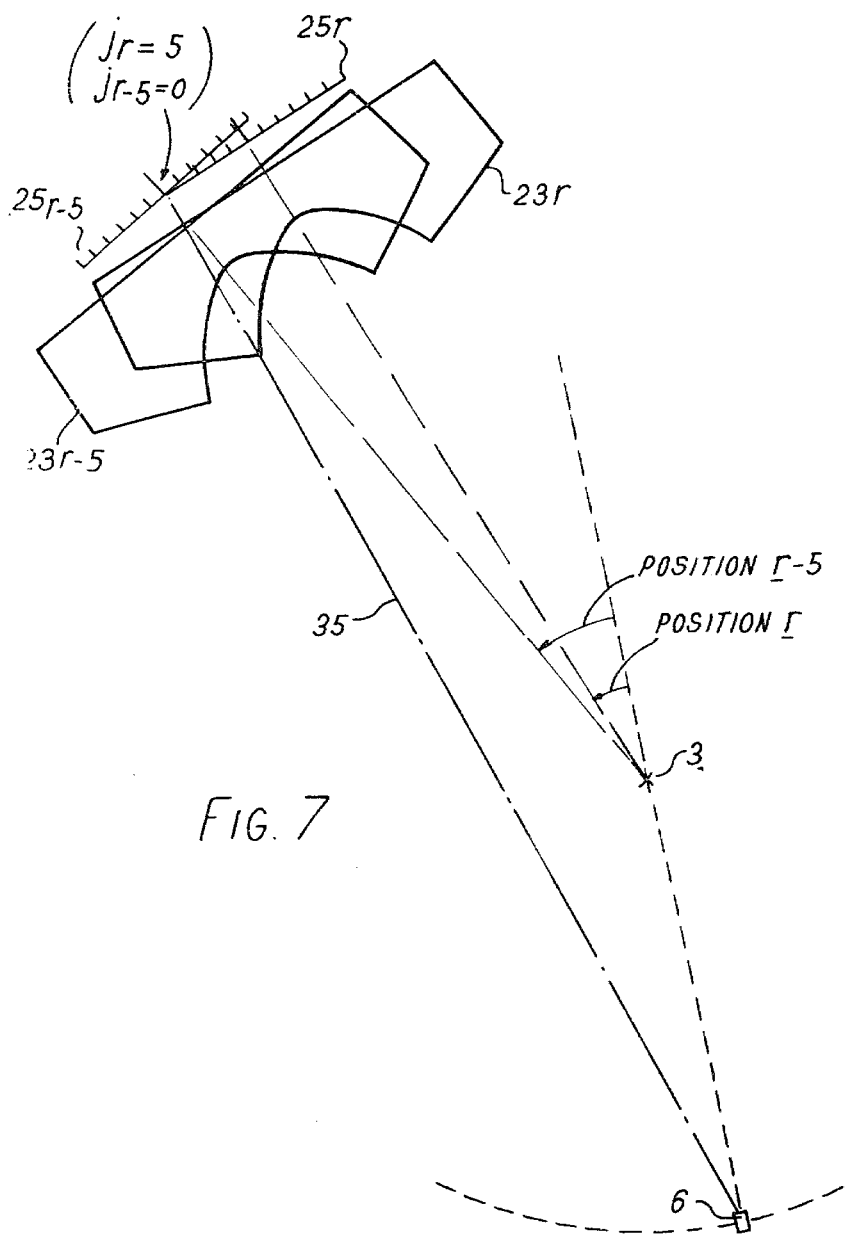

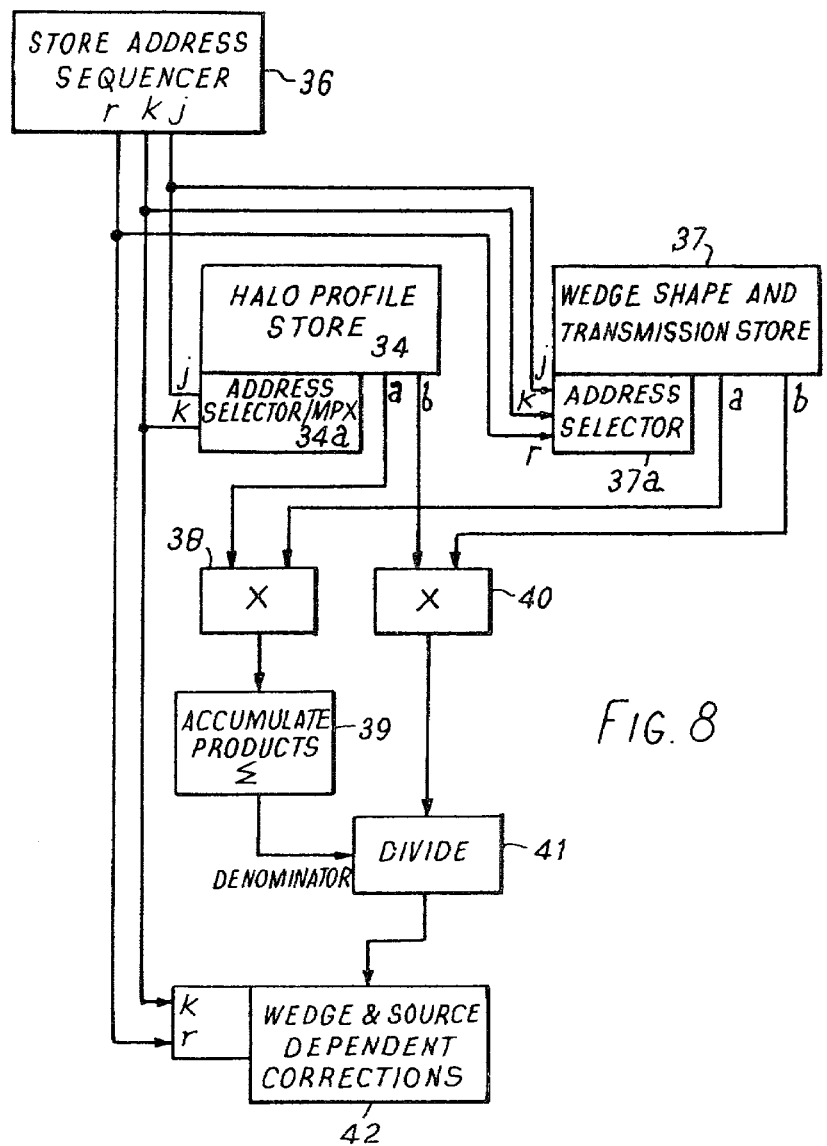

MEDICAL RADIOGRAPHIC APPARATUS AND METHOD

The present invention relates to medical radiographic apparatus, of the type commonly known as computerised tomographic (CT) apparatus, and to a method of operating such apparatus.

CT apparatus is used for obtaining representations of the variation of absorption of penetrating radiation with position in a selected region, usually a cross-sectional slice, of the body of a patient. Examples of such apparatus are described in U.S. Pat. No. 3,778,614. That patent shows that examination may be rapidly effected by orbiting a source, producing a substantially planar fan shaped distribution of x-rays, around the patient and detecting the radiation transmitted through the patient's body along a plurality of beams within the distribution.

Detection may be by detectors which rotate around the patient in synchronism with the source. However it has been proposed to employ a circular array of static detectors which surround the body to detect radiation from a source which orbits as taught in the said U.S. Patent. That arrangement may be implemented by having the source orbit the body inside the circle on which the detectors are disposed (see U.S. Pat. No. 4,101,768). There is, however, described and claimed in U.S. Pat. No. 4,137,455 an apparatus in which the source moves in an orbit at greater radius than that of the detector circle. Means are provided to prevent detectors which might otherwise lie between the patient and the source from obscuring the patient from radiation. This arrangement has the advantage that relatively less detectors are required. Both of these systems use a fan of radiation which subtends a relatively large angle at the source, for example 50° or more, whereas it has been the practice previously to use narrower spreads of radiation. It has been found that such x-ray sources, typically rotating anode x-ray tubes tend to have radiation emission from regions surrounding the x-ray source spot proper and, because of the required wide fan angle, it is not convenient to eliminate such radiation by the use of anode shields. In many circumstances such off-focus radiation may not be a significant problem. However it is also the practice to place between the source and the patient compensating attenuators (often known as "wedges" although they are in general saddle shaped) which correct the radiation profile for the approximately circular cross-section of a patient's body. Off-focus radiation will pass through such wedges at parts differing in thickness from the parts through which the main examining radiation passes and may be less attenuated than the main beam giving rise to significant errors.

It is an object of this invention to provide an apparatus and method whereby such errors are reduced.

It is another object of the invention to provide computerised tomographic apparatus including: a source of a fan-shaped distribution of radiation, which originates primarily from a region on an x-ray target and in part from a halo region on said target around said first mentioned region and which propagates through a patient position in which a patient to be examined may be disposed: means for moving the source angularly around said patient position, so that the radiation propagates therethrough from a plurality of different directions; a plurality of detector devices for detecting radiation which has propagated through the patient position along a plurality of mutually divergent beam paths from each of said directions, the arrangement being such that the source moves relative to the detector devices to cause each detector device to view the source along a plurality of paths in different directions in the course of the angular movement and to provide output signals each representative of the intensity of radiation received along one of said plurality of paths; attenuator means, disposed between the source and the patient position and moving around the patient position with the source, having an attenuation which is different for beam paths having different path lengths through the body of a patient disposed in the patient position to tend to equalise absorption therein; means for correcting the output signals, or signals derived therefrom, to reduce components thereof representative of radiation, which originated from said halo region received by the detector after passage through the patient's body; and means for processing the modified signals to provide a representation of the absorption of the radiation in a cross-sectional slice of the patients body.

It is another object of the invention to provide a method of operating a computerised tomographic apparatus, in which x-radiation is propagated in a fan shaped distribution from a region of a source at a plurality of positions around the body of a patient so that it passes through the patient and through an attenuator which equalises absorption from paths having different absorbing lengths in the patient, and is incident at a plurality of detector devices, which view the source along a plurality of paths in different directions to provide output signals indicative of the intensity of radiation received along respective paths, the method including correcting the output signals for components resulting from halo radiation which originated not from the said region of the source but from a halo region therearound, by estimating the intensity of halo radiation at each detector and subtracting the estimate from the respective output signal.

It is yet another object of the invention to provide medical radiographic apparatus including: an x-ray tube in which an electron beam is incident on a target member to generate x-rays which propagate in a fan shaped distribution to pass through the body of a patient; a plurality of detectors arranged to receive the radiation after passage through the patient's body and to prove output signals indicative of the intensity of radiation received, for processing to provide a representation of the distribution of attenuation of the radiation in a cross-sectional slice of the patient's body; an attenuating member disposed between the x-ray tube and the patient's body to reduce differences of intensity of radiation received by the detectors after passing through the patient's body along paths of different length; and correcting means for reducing components of the output signals resulting from received radiation which originated not from the region of the target at which the electron beam was incident but was generated at a halo therearound, for example by incidence of secondary electrons on the target.

In order that the invention may be clearly understood and readily carried into effect it will now be described, by way of example, with reference to the accompanying drawings, of which:

Figure 9:
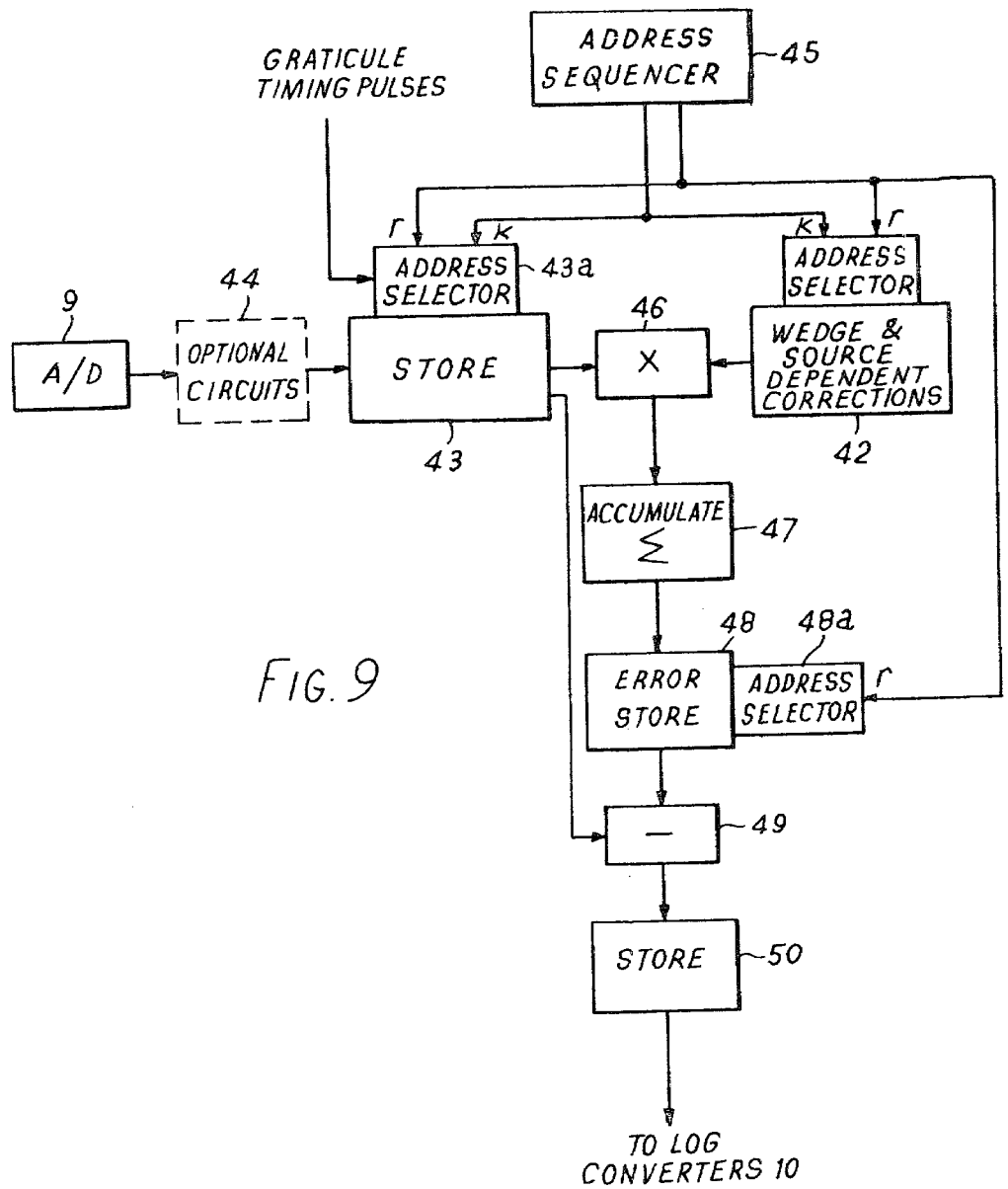

FIG. 3 illustrates the effect of an attenuating wedge on radiation from a wide angle source, FIGS. 4a and 4b are used to explain two methods of assembling fans of x-ray beams, FIGS. 5a, 5b and 5c are profiles for halo radiation from the x-ray source viewed from different directions after attenuation by the wedge, FIG. 6 shows how the profiles of halo radiation prior to attenuation by the wedge is are measured, FIG. 7 is used to explain the geometry of the apparatus and the significance of radiation received by a detector from different directions, FIG. 8 is a block diagram of circuits for determining correction terms prior to examination of a patient, and FIG. 9 is a block diagram of circuits used to correct output signals measured for the body of a patient being examined.

A CT system of the type disclosed in U.S. Pat. No. 4,137,455 is shown in simplified form in FIG. 1. A source 1 of a fan of x-rays 2 orbits about an axis 3 which lies in a region in which a patient 4 is disposed, approximately on the axis. The patient 4 is supported on a couch or platter 5. Around the patient 4 is disposed a ring 6 of detectors, of which only some are shown. The radiation from the source 1 is intercepted by detectors on the opposite side of the patient. The detectors are stationary and, as the source rotates the radiation moves over the detectors and irradiates different ones of them. Means, not shown but described in U.S. Pat. No. 4,137,455, are provided to prevent the radiation being intercepted by the detectors closest to the source although the effect can be achieved by putting the source inside the detector ring.

The signals provided by the detectors represent the radiation transmitted through the patient along individual narrow beams, as defined by the detectors apertures and source motion in the time required to obtain a reading. They are taken to amplifiers 7. An individual amplifier is, in principle, required for each detector. However, in practice, the detectors are not all irradiated at the same time, and some multiplexing of outputs is possible, with consequent savings in equipment. The signals are then integrated in integrators 8 for a period which represents one beam of radiation as received by that detector, taking into account the source motion in that time. The required timing signals are provided by source position indicators, not shown, such as a transparent substrate, mounted to rotate with the source, carrying graticule markings to interrupt a light path between a light source and photocell.

The detector signals are then subject to conversion to digital form in analogue-to-digital converters 9 and are converted to logarithmic form in converters 10, in which form they are provided to processing circuits 11.

The circuits 11 may process the signals as described in U.S. Pat. No. 3,778,614 or by a development of that procedure involving a form of convolution, described in U.S. Pat. No. 3,924,129. This may be a convolution processing requiring signals for sets of parallel beams of radiation, in which case the signals must be presorted into the correct sequence. The preferred processing, however is one which is appropriate to signals for sets of beams distributed in the form of a fan.

The processed data are finally displayed on suitable equipment such as a T.V. monitor or line printer or stored for future use, on equipment indicated generally at 12.

Figure 1:
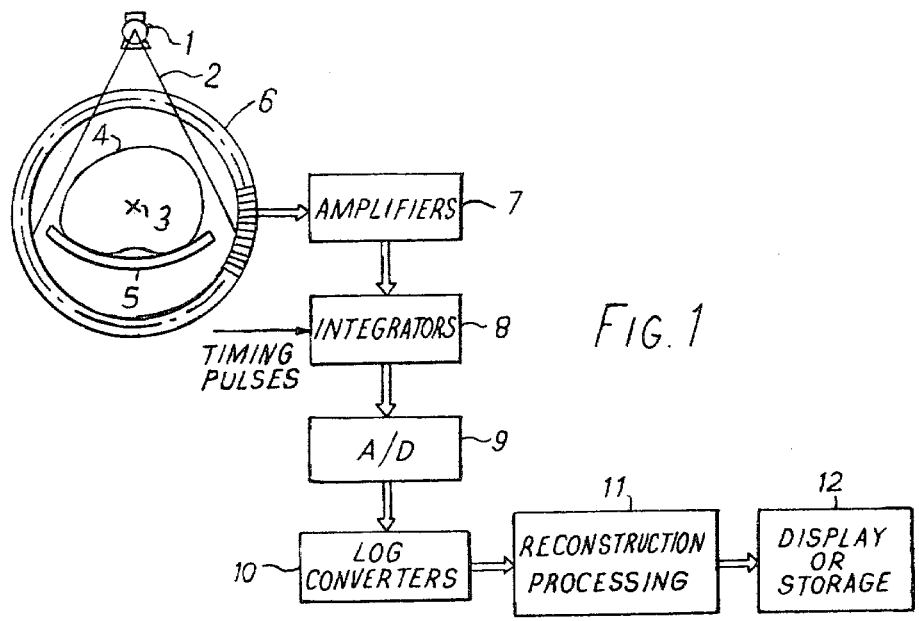
FIG. 1 shows in schematic form an apparatus with which the invention may be used.
Figure 2:
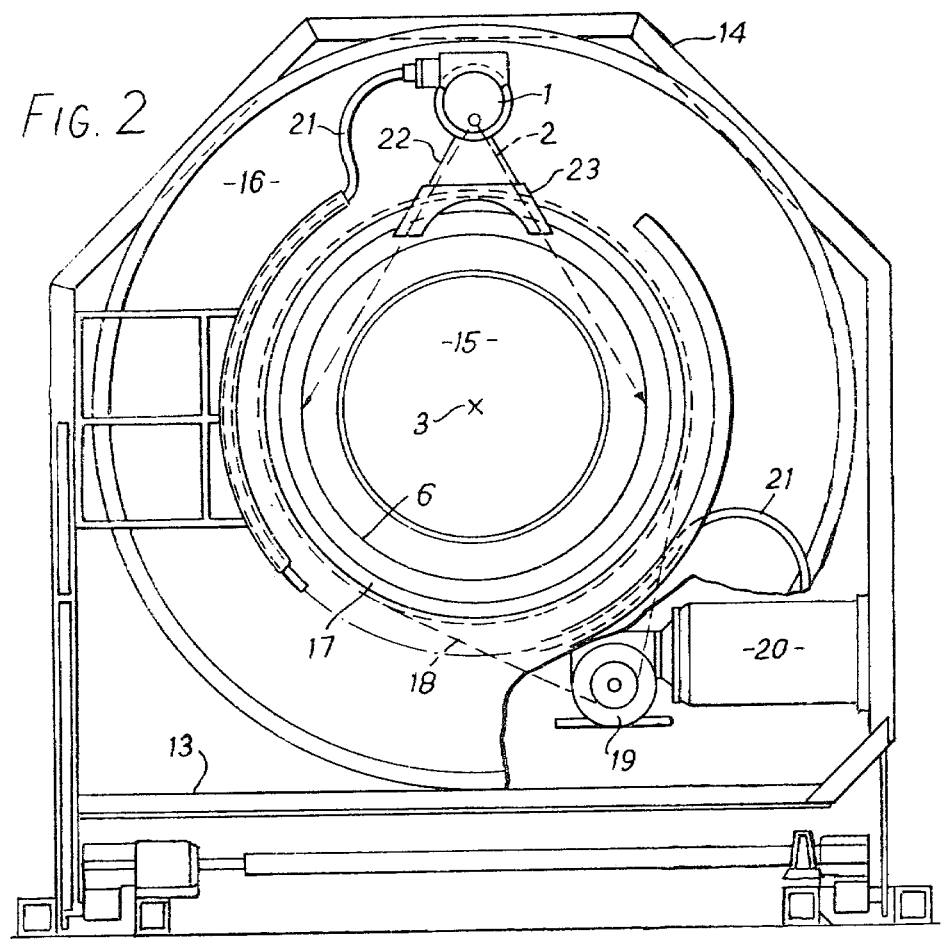
FIG. 2 shows one view of the scanning part of the apparatus of FIG. 1.

FIG. 2 shows an end elevation of the scanning equipment used to obtain the detector signals. Those elements shown in FIG. 1 are identified by the same reference numerals. The apparatus is mounted on a main frame 13 covered by an outer cover 14, these being mounted in a suitable manner. Frame 13 and cover 14 have an aperture 15 to admit the patient. The x-ray tube 1 is supported on a member 16 which is rotatable about axis 3 on bearings 17. Member 16 is driven, via a belt 18 and gearbox 19, by a motor 20 mounted on the main frame. Power supplies and cooling oil to the x-ray tube 1 are carried by cables 21, which are of sufficient extent and have a suitable cable handling arrangement to allow the tube to orbit through a working 360° plus, say, 180° to come to working angular velocity and, say, 180° to stop.

Mounted below the source 1, to share in its rotation, are a collimator 22, which constrains the beam 2 to the required fan-shape, and a compensating 'wedge' 23 mentioned hereinbefore. The wedge 23 is intended to compensate for the fact that the patient, with the couch and any packing materials used, tends to have an approximately circular cross-section, so that radiation travelling along paths close to the centre of the patient's body passes through a longer absorbing path, and consequently would be detected with less intensity, than radiation passing through the edge of the body. The wedge provides a longer absorbing path to the outer beams and therefore tends to equalise the intensity with advantages including that all detectors operate in the same part of their range.

In general the use of a wedge provides few problems to apparatus employing an x-ray tube which produces radiation from a substantially point source although some corrections are required for variations in the hardness of the radiation caused by the different paths through the wedge.

X-ray tubes used in CT equipment have often produced fan distributions of radiation having relatively narrow angles and these are sufficiently close to being point sources. However this result is in part obtained by placing shields around the x-ray anodes to prevent the emission of "off focus" radiation, initiated by secondary electrons incident on the anode, which radiation provides in effect a 'halo' around the main source spot. Where x-ray tubes are required, as for the apparatuses of the said U.S. Pat. Nos. 4,101,768 and 4,137,455, to provide fans of wide angle (typically 50°) it is difficult to provide such a shield. This problem is exacerbated where rotating anode x-ray tubes are used. Thus the radiation includes a main emission from a well defined source spot on the anode and a more diffuse and less intense 'halo' of radiation from the anode surface around the spot.

The effect which the halo of radiation has in combination with the compensating wedge is shown diagrammatically in FIG. 3. An x-ray target or anode is indicated by the line 24, although in practice it is generally a known type of rotating anode tube. The target 24 emits radiation with an intensity distribution indicated by the curve 25. This has a central peak of emission from point 26 with a surrounding halo of lower intensity. The radiation passes through the compensating wedge 23 to be incident on detectors 6. The radiation across the 50° fan is, of course, incident on a large number of the detectors but consideration will first be given to the radiation incident on a detector $6_a$ opposing the source, i.e. at the centre of the fan. A beam 27 from the central peak is shown together with beams 28 and 29 from the edges of the halo and it will be seen that beams 28 and 29 have longer paths through wedge 23 than beam 27 and are further attenuated. Thus the contributions to the signal from detector $6_a$, from different positions on anode 24 are given by curve 30 from which the halo contributions are reduced.

However taking a detector $6_b$ at the edge of the fan and typically centre and edge beams 27′, 28′ and 29′, it will be seen that centre beam 27′ now has actually a longer path through the wedge 23 than beam 29′ which is a halo component. The contributions to the signal from $6_b$, from different positions on the anode 24 are given by curve 30′ in which the halo contribution is asymmetrical and in places relatively high. This means that absorbing material in the body which intercepts beam 29′ but not beam 27′ can have a large effect on the output signal from detector $6_b$ although it should have no effect.

It is proposed that the problem be reduced by reversing wedge 23 and placing it closer to the axis 3. It can then achieve the same path length compensation with a gentler curve, the effect being shown somewhat exaggerated at 23′. However this step merely reduces the problem but does not eliminate it.

It should be understood, for the purposes of the following description, that when in CT reference is made to a fan distribution of x-ray beams passing through a patient such a fan may take two forms. The first form, illustrated schematically in FIG. 4a, most commonly used as an example is one in which a fan of beams emanating from one position of the source 1 are incident simultaneously on a plurality of detectors such as $6_{(n-1)}$. The detector output signals simultaneously measured thus are for a fan of beams emanating from one source position and signals measured at different times are for similar fans at other angular orientations.

An alternative arrangement possible when detectors do not orbit with source 1 and shown schematically in FIG. 4b, is to select from the radiation emitted at each of a plurality of positions of sourse 1 in its orbit, such as $1_{(n-1)}$, $1_n$ and $1_{(n+1)}$, the beam incident on a single detector $6_n$. Over several source positions the output signals measured in sequence are for a fan of beams converging on the position of detector $6_n$. Of course the output signals have to be reordered to achieve this effect and are not available at one time. However at the same time output signals are measured for fans of beams converging on other detector positions. There are certain advantages in this procedure and the following description will be given on the understanding that a fan of beams is a 'detector fan' as shown in FIG. 4b although it is applicable to 'source fans' as in FIG. 4a.

Considering the distributions of the origin of radiation received by a detector from one source position, as shown in FIG. 3 at 30 and 30′, it will be seen that each of these is a combination of the radiation from the centre spot and that from the halo, each as modified by the wedge. The effect of the wedge on the centre spot (or rather the main beam of radiation emitted from that spot) is, of course, intended and is the purpose of the wedge. As each detector follows the source through the series of positions giving one detector fan, the function for the halo part will change from the halo component of 30′ through that of 30 to the mirror image of 30′ at the opposite extreme. These are shown in FIGS. 5a, 5b and 5c respectively.

It is proposed to modify the readings taken by the detectors with correction terms derived from the measured shape of the halo profile 25 and the known shape and composition of attenuator 23, to provide detector signals for which the halo component is removed, at least in part.

The detector signals to be operated on are taken to be those provided by one detector for a detector fan of beams and the procedure is repeated identically for other such fans. It will be assumed that for each position, at which the detector views the source to give an output signal, there has been derived an emission profile for the halo without the wedge being present. It is desired to determine the proportion of each detector output signal provided by the halo radiation after passage through the wedge and the body. It will be appreciated that to achieve this rigorously it is necessary to know the absorption of the halo radiation by the body. It is, of course, that absorption which the CT apparatus is intended to evaluate. The detector output signals themselves provide in effect a first estimate of that absorption for the detector fan being evaluated if the attenuation imposed by the wedge is compensated. The output signals are themselves corrupted by the halo radiation but they provide a sufficient first estimate of the bodies absorption for correction purposes. The correction terms of 2n+1 values are processed (in a manner to be described hereinafter) with the detector output signals either side of that being evaluated and the result is the halo error component.

This process is similar to a convolution of two functions one of which is derived from the measured intensity readings and the other being spatially variable and derived from the measured halo profile and the known form of the attenuator 23. The halo error component is then subtracted from the output signal to give a halo corrected value. It is proposed that this first corrected value is sufficiently accurate to proceed to the processing which yields the final picture. However it may be advantageous to modify the process described to produce a repetitive process which, on each iteration produces a more accurate estimate of the attenuation of radiation by the body, and hence a more accurate estimate of the halo error component.

It will be understood that the attenuation coefficient of the wedge $\mu_w$ and the absorbing path lengths through the wedge $x_w$ are known, as design parameters. These, together with the extent of the halo for the x-ray tube being used and the dimensions of the apparatus may therefore be stored for use as required and the halo profile may then be calculated as necessary.

It is nevertheless convenient to measure the halo profiles for a sufficiently large number of relative positions of source and detector, in the absence of a body and with the wedge 23 removed. The manner of obtaining a profile for one detector position is shown in FIG. 6.

It will be understood that the halo profile observed for one detector, as the anode 24 passes across its field of view during source rotation, will be exactly the same as that observed by any other detector, in the absence of any other considerations. It is therefore only necessary to measure the profile for one typical detector. As shown in FIG. 6, a test piece 31 is placed before the detectors so as to obscure all but one detector 6 but to allow radiation to fall on that detector by a narrow slit 32 along a narrow beam line 33. With the wedge attenuator 23 removed and no body present, the x-ray tube including anode 24 orbits about the axis of rotation in the normal manner, such that profile 25 passes over the reading beam line 33. The profile is then recorded in successive samples by the detector 6. The profile readings are then stored in a halo profile store 34.

This procedure is part of the precalibration procedure which only needs to be carried out once for the x-ray tube in use, or it may be repeated if the tube characteristics may have changed. It may, therefore, use specially set up circuits. It is an advantage, however, to use the normal detector output signal handling circuits so that the halo profile is sampled, in response to graticule timing pulses, at the same intervals as in a normal scan.

It should be noted that it may be advantageous also to correct the recorded halo profile for the effects of the finite width of beam line 33.

The profile is stored in store 34 as an intensity value $I_o^o$ for the main beam spot and a number of samples either side of that spot each being identified as $I_j^o$, where typically $-27 \leq j \leq 27$.

In considering the use of the measured profile it is convenient to label the position of the source relative to the detectors and for the purposes of this example of the invention this will be by an integer r. FIG. 7 shows the position of the source, indicated by the halo profile $25_r$, and the attenuating wedge $23_r$ at position r relative to the line through the axis from an arbitrary detector 6. The integer r represents the orbital position of the source such that rotation through one integer takes place in one detector integration period. The halo profile $25_r$ is indicated as discrete sampled values, as provided by the arrangement of FIG. 6, in FIG. 7 with six values either side of the main spot although, as mentioned hereinbefore, the typical samples are twenty seven.

If the halo sampling is, as described, at normal detector sampling intervals than the spacing of the halo samples j corresponds to the rotational positions r. Thus for halo and wedge at position r−5 (illustrated as $25_{r-5}$ and $23_{r-5}$ respectively) the centre beam from the main spot, j=0, travels to detector 6 along the same path 35 as that travelled by radiation from the halo at j=−5 for position r.

Considering now the nature of the error and its correction in more detail, it will be realised that the intensity recorded at detector 6 for position r of the source is the sum of the intensities of x-rays originating at each of the (in this example) 55 sampled positions of the halo ($-27 \leq j \leq 27$) after they have been attenuated by the wedge on their respective paths therethrough and by the patient's body when a patient is present. It should, of course, be only for radiation emitted at the main spot (j=0) and it is desired to determine the proportion originating elsewhere (j≠0) and to subtract it from the measured signal.

The attenuation in the patient along the paths from the halo can in effect be measured but for the moment it is convenient to make the assumption that it is the same for all paths from the halo to the detector at any one source position. Then the attenuation along this assumed common patient path can be taken to be the signal provided by the detector (i.e. the total radiation received from halo and main spot) divided by the sum of the intensities of the source samples multiplied by their respective attenuations in the wedge (i.e. the total halo and main spot radiation immediately after the wedge). Since the halo samples have been measured as described in relation to FIG. 6 and since the wedge is a material (usually Aluminum) of known attenuation coefficient it is straightforward to determine attenuation along each path therethrough and hence the required divisor.

When the attenuation along this assumed common path through the patient has been determined it is assumed to be correct for the centre path from the main spot. However as explained in relation to FIG. 7, the path from the main spot (j=0) for position (r−n) is the same as that from halo sample j=−n for position r. Using this, the attenuation along the patient path for halo sample j=−n at position r is given by the detector output reading at position (r−n) divided by the sum of halo intensities after passage through the wedge at position (r−n).

Thus the contribution, to the detector output measured, from halo sample j=−n position r is the source intensity at position −n of the halo multiplied by attenuation in the wedge, further multiplied by the detector total reading at position (r−n), all divided by the sum of the source intensities after the wedge at position (r−n).

The total correction is then given by summing these contributions over a range of detector readings either side of that being corrected for source positions from (r−k) to (r+k) not including the contribution for k=0 which would be equivalent to using the detector reading to correct itself.

This correction has been evaluated by making certain assumptions which are believed to be justifiable in practice, rather than by exact mathematical analysis. Nevertheless it can be expressed for clarity of explanation by the following equation:

$$O^r = \sum_{\substack{k=-27 \\ k \neq 0}}^{27} \left[ \frac{I_k^o e^{-\mu_w x_w^{k,r}} I_{Det}^{r+k}}{\sum_{j=-27}^{27} [I_j^o e^{-\mu_w x_w^{j,r+k}}]} \right] \quad (1)$$

In the foregoing equation $O^r$ is the error term to be subtracted from the reading of a detector at source position r.

$I_{Det}^{r+k}$ is the reading from a given detector of radiation transmitted through the patient's body for position (r+k) of the source. This reading is uncorrected for halo error but is in practice aften already corrected for other errors.

$\mu_w$ is the linear attenuation coefficient of the homogeneous wedge (usually aluminium).

$X_w^{k,r}$ is the path through the wedge of the rays emanating from the kth sample of the halo for the r'th position of the source and $I^o_k$ is the relative intensity of the kth sample of the halo.

In the above only $I_{det}^{r+k}$ requires the presence of the patient for its determination. The correction can therefore be separated into $$O^r = \sum_{\substack{k=-27 \\ k \neq 0}}^{27} P_k^r I_{det}^{r+k} \quad (2)$$

where $P_k^r$ is the k'th entry of the rth profile given by $$P_k^r = \frac{I_k^o e^{-\mu_w x_w^{k,r}}}{\left[ \sum_{j=-27}^{27} I_j^o e^{-\mu_w x_w^{j,r+k}} \right]} \quad -27 \leq k \leq 27 \quad k \neq o \quad (3)$$

all of the terms in (3) being capable of evaluation as part of the setting up procedure in the absence of any body in the apparatus and being held in store until required in an examination.

Circuits for achieving these parts of the correction are shown in FIG. 8. The halo profile measured in the procedure, described with reference to FIG. 6, is held in a store 34. The storage locations used were chosen by the address selector 34a according to the value of integer j ($-27 \leq j \leq 27$ in this example) from the centre main spot for which j=0. Similarly address selector 34a selects the signals for output in response to values of integer j or integer k from store sequence addresses 36. j and k have similar significance in relation to the number of a halo sample from the main spot. The significance of j is, however, solely in terms of counting across the halo profile to use different samples. The significance of k is in terms of the use of a detector output reading for which the position is r+k so that a halo component from sample k is seen by the detector. In view of their different significance j and k are entered and counted separately.

A wedge shape and transmission store 37 holds information defining the shape of the attenuating wedge 23 (in more complex cases several such wedges for different patient sizes) its attenuation coefficient and the path length through the wedge for all paths to be used. A path from a halo sample to any detector is defined by the current values of j, k and r. The attenuations for the paths can be precalculated and stored and in response to the appropriate inputs from address-sequencer 36 the store 37 supplies at its output the attenuation in the wedge 23 for the path identified.

Although in this example a single halo profile is measured and the attenuation paths through the wedge are prestored in 37, it is of course possible to measure the profile with the attenuating wedge inserted in the arrangement of FIG. 6. In that case store 34 would hold not one profile but a large number measured for all directions from which the detector 6 views the source through the wedge. This alternative would eliminate store 37 but is considered in practice to be less efficient.

It may be noted that it is now common practice when using such wedge attenuators to correct for beam filtration in the wedge by materials such as aluminum. Although it does not form part of this invention the attenuation values provided by store 37 can be precalculated to include such a correction.

The circuits of FIG. 3 first determine the denominator of Equation (3) for one value of k, that is to say the total photon flux main beam and halo, received by the detector with no body present when the source is at position r+k. Address sequencer 36 provides the values of r and k at which it is preset to commence and counts one at a time through each value of j for which halo profile store 34 holds a non-zero value ($-27$ to $+27$). At each j value, store 34 provides the halo sample and store 37 provides the wedge path attenuation at outputs a. These are multiplied in a multiplier 38 and accumulated in a store 39 for all of the values of j. For the numerator of equation (3) sequencer 36 sets selects from 34 the halo sample k and its wedge path attenuation from 37. These are provided at outputs b as a result of the sequence in j being complete and are multiplied in a multiplier 40 to give the total x-ray flux due to element k of the halo as attenuated by the wedge and on route to corrupting the main beam output signal for source position r. The ratio of these two fluxes is provided by a dividing circuit 41 and is a value of $P_k{}^r$ which is stored in store 42 for future use. The value of k is stepped by one and the procedure is repeated for values of k limited by the extent of the halo profile values in 34 (but not for k=0).

As mentioned the process of FIG. 8 is carried out as a calibration procedure before examination commences. Although the circuits shown are suitable for use in practice it will be apparent that all the values held in store 42 could have been precalculated when the halo profile had been measured and entered in a suitable store for further use.

During examination of a patient the corrections are implemented by circuits shown in block diagrammatic form in FIG. 9.

The detector output signals supplied by Analogue to Digital converters 9 are entered into a temporary store 43, which may be a random access memory (RAM). The storage location at which they are entered are determined by address selector 43a in response to graticule timing pulses. The addresses are determined in a predetermined manner which, as in prior art apparatus will be effective to arrange the signals in order as "detector fans" if this is required for the form of reconstruction processing to be used. The locations for reordered signals for each fan are identified by integers r and k as explained hereinbefore. Up to and including the storage in store 43 the procedure is that known for apparatus currently available and may include other optional circuits, perhaps for other corrections of known form, indicated in broken outline at 44.

To implement this invention each signal in store 43 is to be withdrawn and have subtracted from it the k readings either side of it in the same fan multiplied by the correction terms in store 42, as explained with reference to equation (2).

The circuit operation is controlled by r and k integer values from an address sequencer 45. This is preset to start at an initial value of r for which the first error component is to be accumulated. It then sequences k through the range of values from $-N$ to $+N$ (not including zero) the range for which wedge and source dependent corrections are held. At each value of integer k the outputs from stores 43 and 42 are multiplied in a multiplier 46 and the total for the full range of k is accumulated in an accumulating store 47 and the accumulated error value entered into a store 48 at address r.

The process is repeated for all relevant values of r for the fan being corrected. Finally k is set to zero and r is sequenced through its range for that fan providing each measured detector output signal in turn to a difference circuit 49 at which the error signal for the same r value from store 48 is subtracted therefrom. The corrected detector signals are entered into a temporary store 50 before being supplied to log converters 10 and subsequent processing.

It has been assumed hereinbefore that a halo profile should be measured and stored for each relative position of source and detector at which an output signal is derived. It will be clear, however, that a small relative movement of the source and detectors will only give a small change in the halo profile. Thus each profile may be used for several, say three, relative positions with consequent savings in storage. Similarly the halo profile of 2N+1 readings may be provided with less accuracy as (2N+1)/m readings, each of which is repeated m times (typically m=3). It should be noted, however, that this reduction of storage can properly only be used if the halo profile has a smooth wide contour and if interpolation is used to supplement the missing profile terms.

As described the invention is implemented with special purpose circuits dedicated to the required procedure. It is common to provide CT equipment with digital computers to perform many of the tasks required and to control the sequence of operation. It should be understood that this invention may readily be implemented by appropriate design or programming of such computers.

Other embodiments of the invention, perhaps to suit a particular processing procedure or design of CT apparatus, may readily be devised by those with the appropriate skills.

What we claim is:

1. Computerised tomographic apparatus including: a source of a fan-shaped distribution of radiation, which originates primarily from a region on an x-ray target and in part from a halo region on said target around said first mentioned region and which propagates through a patient position in which a patient to be examined may be disposed; means for moving the source angularly around said patient position, so that the radiation propagates therethrough from a plurality of different directions; a plurality of detector devices for detecting radiation which has propagated through the patient position along a plurality of mutually devergent beam paths from each of said directions, the arrangement being such that the source moves relative to the detector devices to cause each detector device to view the source along a plurality of paths in different directions in the course of the angular movement and to provide output signals each representative of the intensity of radiation received along one of said plurality of paths; attenuator means, disposed between the source and the patient position and moving around the patient position with the source, having an attenuation which is different for beam paths having different paths lengths through the body of a patient disposed in the patient position to tend to equalise absorption therein; means for correcting the output signals, or signals derived therefrom, to reduce components thereof representative of radiation, which originated from said halo region received by the detector after passage through the patient's body; and means for processing the modified signals to provide a representation of the absorption of the radiation in a cross-sectional slice of the patients body.

2. An apparatus according to claim 1 wherein the means for correcting includes a store holding a profile of radiation received by a detectors from different paths of said halo region for different dispositions of the detector relative to the source and means for modifying each output signal, or signal derived therefrom, in dependence on the profile.

3. An apparatus according to claim 2 wherein the means for correcting includes utilising the halo profile and estimates of the attenuation imposed by the attenuator means on the radiation to derive correction signals from which said components can be derived.

4. An apparatus according to claim 3 wherein the means for modifying includes means for multiplying the correction signals with a plurality of output signals, for beam paths either side of that giving rise to the output signal being corrected, to give an accumulated error signal and means for subtracting the error signal from the respective output signal.

5. A method of operating a computerised tomographic apparatus, in which x-radiation is propagated in a fan shaped distribution from a region of a source at a plurality of positions around the body of a patient so that it passes through the patient and through an attenuator means which equalises absorption from paths having different absorbing lengths in the patient, and is incident at a plurality of detector devices, which view the source along a plurality of paths in different directions to provide output signals indicative of the intensity of radiation received along respective paths, the method including correcting the output signals for components resulting from halo radiation which originated not from the said region of the source but from a halo region therearound, by estimating the intensity of halo radiation at each detector and subtracting the estimate from the respective output signal.

6. A method according to claim 5 in which the said estimate is achieved by measuring, for a plurality of directions from which a detector may view the origin of the radiation, the distribution of emission of halo radiation at different positions in the vicinity of the said region of the source and modifying the intensity of the halo radiation to take account of attenuation by the attenuator means and by the patient's body.

7. A method according to claim 6 in which the profile of emission of halo radiation is combined with determinations of the attenuation imposed on the radiation by the attenuator means on different paths therethrough to derive correction terms indicative of the extent of halo radiation incident on the body.

8. A method according to claim 7 in which the correction signals are multiplied by a plurality of output signals for beam paths either side of that giving rise to the output signal being corrected and the products accumulated to provide the said estimate.

9. A method according to claim 8 in which the correction procedure is repeated using the first corrected output to more accurately determine the said estimates.

10. A method according to claim 6 in which the profile of the emission of halo radiation is obtained at each direction from which a detector may view the origin of the radiation by placing an aperture centrally to the field of view of the detector and measuring the radiation received at each of a plurality of positions of the source as it moves across the aperture.

11. Medical radiographic apparatus including: an x-ray tube in which an electron beam is incident on a target member to generate x-rays which propagate in a fan shaped distribution to pass through the body of a patient; a plurality of detectors arranged to receive the radiation after passage through the patient's body and to provide output signals indicative of the intensity of radiation received, for processing to provide a representation of the distribution of attenuation of the radiation in a cross-sectional slice of the patient's body; an attenuating member disposed between the x-ray tube and the patient's body to reduce differences of intensity of radiation received by the detectors after passing through the patient's body along paths of different length; and correcting means for reducing components of the output signals resulting from received radiation which originated not from the region of the target at which the electron beam was incident but was generated at a halo therearound, for example by incidence of secondary electrons on the target.

12. An apparatus according to claim 11 including means for providing a movement of the x-ray tube relative to the detectors so that each detector views the origin of the radiation from a plurality of different directions and wherein the correcting means includes means storing estimates of radiation generated at said halo and attenuated by said attenuating member to be received at a detector at respective ones of said different direction; means for modifying the estimates to take account of absorption of the halo radiation by the patient's body; and means for deducting the modified estimates from the respective output signals.

13. An apparatus according to claim 12 in which the means for modifying includes means for combining the estimates with uncorrected output signals for paths close to that for which the output signal is being corrected.

14. An apparatus according to claim 13 in which the means for combining is arranged to multiply the estimates by the said uncorrected output signals and accumulate the products thereof.

* * * * *

UNITED STATES PATENT AND TRADEMARK OFFICE
CERTIFICATE OF CORRECTION

PATENT NO. : 4,250,387
DATED : February 10, 1981
INVENTOR(S) : Godfrey N. Hounsfield et al.

It is certified that error appears in the above-identified patent and that said Letters Patent are hereby corrected as shown below:

Column 2, line 46, delete "prove" and insert -- provide --.

Column 3, line 9, after "wedge" and before "are" delete -- is --.

Column 5, line 40, delete "sourse" and insert --source --.

Column 8, line 45, delete "aften" and insert -- often --.

Column 11, line 27 (Claim 1), delete "devergent" and insert -- divergent --.

Column 11, line 39 (Claim 1), delete "paths" and insert -- path --.

Column 11, line 52 (Claim 2), delete "detectors" and insert -- detector --.

Column 11, line 52 (Claim 2), delete "paths" and insert -- parts --.

Signed and Sealed this

Seventh Day of September 1982

[SEAL]

Attest:

GERALD J. MOSSINGHOFF

Attesting Officer    Commissioner of Patents and Trademarks